United States Patent
Allaf et al.

(10) Patent No.: US 6,551,644 B1
(45) Date of Patent: Apr. 22, 2003

(54) METHOD FOR TREATING VARIOUS PRODUCTS

(75) Inventors: Karim Allaf, La Rochelle (FR); Zoulikha Maache-Rezzoug, Victor (FR); Sidahmed Rezzoug, La Rochelle (FR); Amel Habba, Courbevoie (FR); Espérance Debs Louka, La Rochelle (FR); Gérard Abraham, La Yerue (FR); Nicolas Louka, La Rochelle (FR)

(73) Assignee: Karim Allaf (FR)

( * ) Notice: Subject to any disclaimer, the term of this patent is extended or adjusted under 35 U.S.C. 154(b) by 0 days.

(21) Appl. No.: 09/638,767

(22) Filed: Aug. 15, 2000

Related U.S. Application Data

(63) Continuation of application No. PCT/FR99/00369, filed on Feb. 18, 1999.

(30) Foreign Application Priority Data

Feb. 19, 1998 (FR) .............................. 98 02032
Sep. 4, 1998 (FR) .............................. 98 11106

(51) Int. Cl.⁷ ................................................. A23L 3/00
(52) U.S. Cl. ........................ 426/521; 426/511; 426/524
(58) Field of Search ................................ 426/521, 510, 426/524, 243, 511; 99/470

(56) References Cited

U.S. PATENT DOCUMENTS

| | | | |
|---|---|---|---|
| 2,278,469 A | | 4/1942 | Musher |
| 3,608,470 A | * | 9/1971 | Zabiyakin et al. ............. 99/470 |
| 4,388,857 A | | 6/1983 | Korek |
| 5,188,856 A | | 2/1993 | Hinz et al. |
| 5,334,402 A | * | 8/1994 | Ovadia .......................... 99/470 |

FOREIGN PATENT DOCUMENTS

| | | |
|---|---|---|
| DE | 34 17 125 A1 | 11/1985 |
| EP | 0 252 155 A1 | 1/1988 |
| EP | 0 406 650 A2 | 1/1991 |
| EP | 0 421 902 A1 | 4/1991 |
| FR | 2 618 981 A1 | 2/1989 |
| FR | 2 638 333 A1 | 5/1990 |
| FR | 2 656 547 A1 | 7/1991 |
| FR | 2 712 206 A1 | 5/1995 |
| GB | 759478 | 10/1956 |
| JP | 62 195250 A | 8/1987 |
| WO | WO 95/04466 | 2/1995 |

* cited by examiner

Primary Examiner—George C. Yeung
(74) Attorney, Agent, or Firm—Piper Rudnick LLP

(57) ABSTRACT

The present invention pertains to a process for the thermal, thermomechanical, hydrothermal or hydrothermomechanical treatment of various natural or transformed alimentary, cosmetic, chemical or pharmaceutical products, in solid, piece, powder, paste, liquid, miscible or nonmiscible liquid mixture, etc. form comprising the precise control of multiple classic thermal processes by accelerating the kinetics, improving the quality of the finished products and reducing the energy consumption and reject rate. These processes generally pertain to the operations of pasteurization, sterilization and/or packaging of solid products in piece or powder form, the thermal modification of the materials (gelatinization, for example), their structure and/or their texture, or the separation of their compounds. The process which is the object of the present invention comprises a step for heating the products to be treated and is characterized by a cooling step based on a pressure drop to vacuum after the heating step.

19 Claims, 3 Drawing Sheets

METHOD FOR TREATING VARIOUS PRODUCTS

RELATED APPLICATION

This is a continuation of International Application No. PCT/FR99/00369, with an international filing date of Feb. 18, 1999, which is based on French Patent Application Nos. 98/02032, filed Feb. 19, 1998, and 98/11106, filed Sep. 4, 1998.

The present invention pertains to a process for the thermal, thermomechanical, hydrothermal or hydrothermomechanical treatment of various natural or transformed alimentary, cosmetic, chemical or pharmaceutical products, in solid, piece, powder, paste, liquid, miscible or nonmiscible liquid mixture, etc. form by application of a cycle of pressure, temperature and/or humidity variation in a treatment chamber.

The treatment has multiple effects; the principal effect attained by the process according to the invention depends on the nature of the initial product introduced into the treatment chamber, the operating conditions employed and the envisaged final product.

BACKGROUND

This invention enables the precise control of multiple classic thermal processes by accelerating the kinetics, improving the quality of the finished products and reducing the energy consumption and reject rate. These processes generally pertain to the operations of pasteurization, sterilization and/or packaging of solid products in piece or powder form, the thermal modification of the materials (gelatinization, for example), their structure and/or their texture, or the separation of their compounds. These effects also include phase separation, especially the extraction of essential oils, fragrances or various components, as well as the improvement of the separation of other compounds (fats, oils, etc.). This treatment improves the quality of the product, especially by the concentration of certain compounds in relation to other constituents. The treatment can facilitate the peeling of fruits and vegetables, improve their pressing, increase the value of their by-products or reduce the number of technical steps in operations, etc. The present invention concerns the precise control of these operations by controlling the temperature and duration of the treatment. The invention also pertains to installations for the implementation of such a process.

Known in the state of the art are many thermal, thermomechanical, hydrothermal or hydrothermomechanical processes for the treatment of biological substances which are designed to modify their qualities.

However, in the various classic operations, the temperature level employed remains routinely limited by the fact that in order to reach the intended objective while still preserving the quality, the higher the temperature employed the more necessary it is to reduce or better control the duration of the treatment.

Nevertheless, the higher the temperature level, the shorter is the required treatment time. But the difficulties in controlling brief durations of treatment and the importance of the relative errors stemming from the durations of heating and cooling considerably reduce the application of relatively elevated temperature levels. Operations of the High-Temperature, Short-Time (HTST) type therefore remain generally a particularly difficult goal to reach outside of the cases of liquid products or products that have a liquid carrier.

The goal of the present invention is to resolve these shortcomings by proposing in the case of all of these operations and all of these envisaged products a very high degree of control of the treatment temperature/duration set of values capable of implementing the operation, accelerating its kinetics and preserving the desired quality of the finished product. The use of high temperature is coupled with a very high degree of control of the duration of treatment by means of a very rapid elevation of temperature and an equally rapid cooling by controlled instantaneous pressure drop down to a determined level of generally reduced pressure. Cooling is thus obtained by self-vaporization of the water and volatile compounds contained in the product because of the descent to vacuum. The final temperature level is primarily a function of the final pressure in the case of a given product.

In most of the envisaged operations and treatments, the mechanical effect is a function of the difference in pressure and temperature before and after the pressure drop and is above all caused by the amount of vapor generated by self-vaporization of the water and other volatile compounds initially present in the product. Its impact, which also depends on the specific thermohydrorheological behavior of the product, can often enable acceleration of numerous envisaged operations and thereby reduce the treatment time. Implementation of a high degree of control over its impact is also facilitated by the intermediary of the high degree of control over the initial pressure and temperature, the final pressure and especially the elapsed time of the pressure drop.

SUMMARY OF THE INVENTION

The present invention consists of providing for a very rapid heating of the product, by specific methods which depend on the product in question, on its form, on its structure and the desired objective, coupled with the imposition of a total pressure "Po". These two operations of heating and application of pressure can be obtained in a coupled manner by injection of dry or wet steam. The operations can also be implemented separately by the use of other heating sources (microwaves, IR, conduction, convection, etc.) coupled with the injection of a suitable gas capable of providing the required high pressure. The invention is characterized in that one then proceeds to a subsequent step comprising a pressure drop down to a lower pressure. The abrupt drop in pressure down to vacuum can be controlled between two limits: the most instantaneous possible pressure drop so as to reduce the cooling time "tr" of the product and, possibly, a rather long pressure drop time in order to reduce the expansion phenomena to a level below 1.5. According to a preferred mode of implementation, the duration of the abrupt pressure drop is a function of the product to be treated, its form, its dimensions and the envisaged quality. It is routinely comprised between instantaneity and several seconds. If the operation of heating and application of pressure is implemented in a chamber, the drop down to the reduced pressure can be obtained by application of a vacuum in the chamber in question by connection to a vacuum tank of relatively large volume, or by mechanical passage of the product into a reduced pressure medium; the two possibilities can also be implemented simultaneously.

The process of treatment by controlled instantaneous pressure drop is known, for example, from the description in French patent FR 93 09 728. This treatment process produces a modification of the texture of the biological product by a rapid expansion of the material. It enables production of expanded products, particularly from fruits or vegetables, which are crisper and more agreeable to eat, or to facilitate their subsequent hydration. The effect produced by this process of the prior art is a significant expansion of the volume to a level larger than 1.5. This application is not relevant to the present invention which is limited to applications that create a very slight expansion of levels routinely lower than 1.5. Nevertheless, the installations which are the object of the present invention can also be used in the process defined by the cited patent.

Also proposed in the prior art was a process for the extraction of juices and fragrances from plant substrates as described in patents FR 26 38 333, FR 88 14 311, FR 89 17 414, FR 92 05 669, FR 93 13 186 and FR 93 13 287. This process is designed for the heating and rapid application of vacuum to a plant material so as to modify its structure and induce the gravitational flow of a juice rich in fragrances with the emission of other aromatic vapors which are recovered separately in the form of condensates. This process is not satisfactory in practice because the energy of the pressure drop is devoted principally to the destruction of the material which facilitates the subsequent extraction by steam distillation. The process which is the object of the present invention concerns precisely the replacement of the steam distillation operation by heating followed by a particularly abrupt pressure drop so as to lead to a self-vaporization operation of various volatile compounds at the final reduced pressure. The self-vaporization of the compounds present according to their thermodynamic properties forms a clear acceleration over steam distillation by the use of the adiabatic and isentropic transformation of the pressure drop down to reduced pressure. The process which is the object of the present invention is thus not linked to the structural breakdown of the material and can also treat mixtures of miscible or nonmiscible liquids as well as plant materials. Here, multiple cycles of heating and pressure drop down to vacuum are therefore often necessary in order to implement the self-vaporization of the mixture of the liquids according to their thermodynamic characteristics and their respective vapor pressures at the treatment temperature.

The applications of the process according to the invention pertain generally to debacterization, pasteurization and sterilization, modification of the structure of the treated materials, separation of their components, preparation of fruits or vegetables so as to facilitate their peeling and/or their pressing, enhance the quality of the finished product or extract, increasing the value of the by-products or reducing the technical steps of the operations, etc. The present invention pertains to the precise control of these treatments by means of controlling the temperature and the duration of thermal, hydrothermal, thermomechanical and hydrothermomechanical treatments.

For this purpose, the present invention in its most general form pertains to a process for the treatment of solid products, especially of biological products in piece, powder or paste form, and of miscible or nonmiscible liquid products, comprising a step of heating the products under pressure for a period of time "tr", characterized in that the process comprises subsequent to the heating step, a step of cooling by pressure drop down to vacuum.

According to a first variant, the heating step is implemented under a pressure greater than or equal to 0.8 bar.

According to another variant, the heating step is implemented by injection of wet or superheated steam.

According to a third variant, the heating step is preceded by a step comprising reduction of the pressure in the treatment chamber, with the pressure before heating being less than 0.2 bar.

According to a fourth variant, the cooling step is implemented by a pressure drop down to a pressure lower than or equal to 0.5 bar.

These different variants are not mutually exclusive and can be combined among each other.

BRIEF DESCRIPTION OF THE INVENTION

Better comprehension of the invention will be obtained by reading the description below regarding nonlimitative examples of implementation of installations according to the invention with reference to the attached drawings in which.

DETAILED DESCRIPTION OF THE INVENTION

Figure 1:
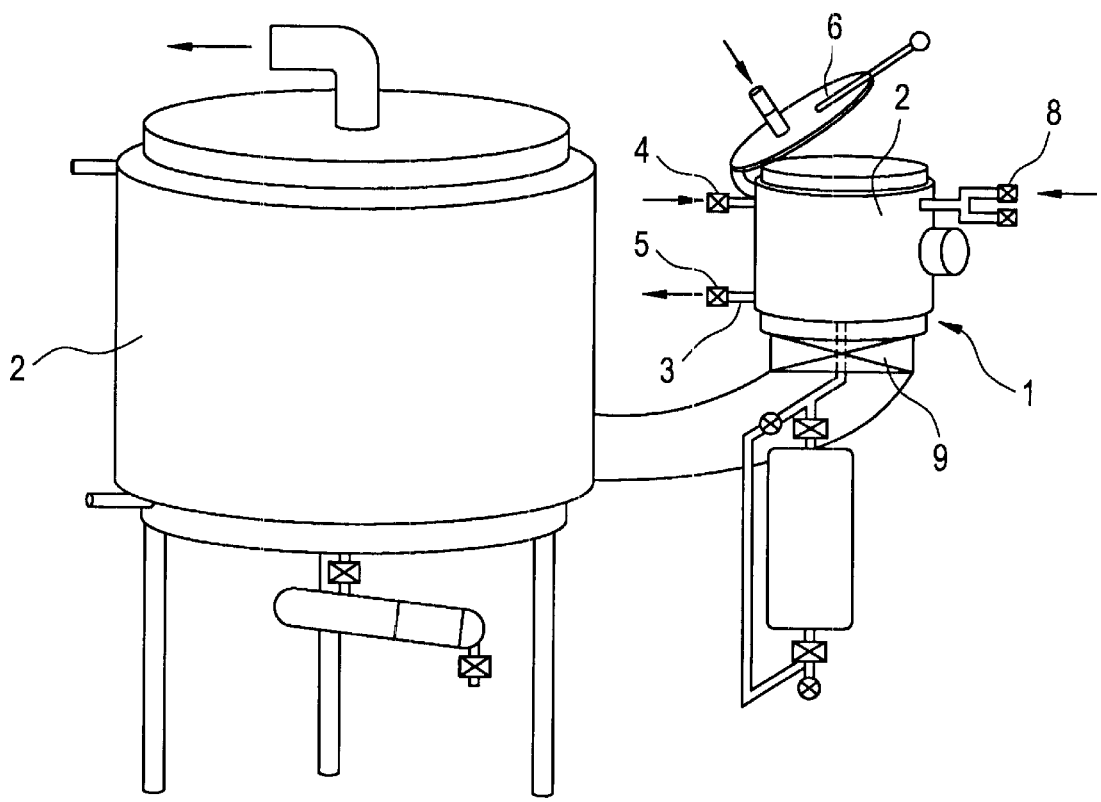
FIG. 1 shows a schematic view of a first variant of implementation of the treatment installation according to the invention.

According to a preferred mode of implementation, an initial step is implemented comprising setting the operating parameters such as the heating temperature level, the duration of heating, the rate of the pressure drop down to vacuum, the value of the various other operating parameters and the temperature and the pressure of the steam in relation to the product to be treated, the organisms and microorganisms to be eliminated and the quality to be preserved and assured.

The operating conditions are preferably determined so as to cause an expansion rate of the treated products that is lower than 1.5 and to cause only a very slight alteration in their texture.

According to a specific mode of implementation, the treatment is localized to the surface of products in piece form, possibly coupled with a reduction in the free surface water of the product.

According to a specific variant, the product is then packaged under vacuum or under neutral gas for its preservation.

One of the applications pertains to the pasteurization, sterilization or debacterization of various liquid or solid biological, alimentary or pharmaceutical products in piece or powder form, for the preparation of products in powder, grain or piece form, solids, liquids or pastes, raw, cooked or semi-cooked, precooked dishes, essential oils, alcohols or pectin, fruits, vegetables, meats, fish, eggs, with varied moisture content or dehydrated, in bulk or prepackaged, debacterized as a result of a defined treatment according to the invention or transformed by controlled thermal, thermomechanical or hydrothermomechanical treatment as defined by the process of the invention.

Known in the state of the art are thermal treatment processes, processes employing radiation such as gamma, ultraviolet or even intense luminous rays, and/or other processes requiring the use of ultrasound. The selection of one or the other of these pasteurization or sterilization methods is based on the type of flora or microorganisms to be destroyed. However, the thermal treatment methods routinely involve a more or less intense alteration of the product to be treated and the destruction of numerous compounds (proteins, vitamins, etc.).

Theoretically, the higher the temperature, the more reduced is this degradation since the required treatment time is clearly shorter. But the difficulties in precisely controlling short durations of treatment and the importance of the relative errors committed in their measurement considerably reduce the use of ultrahigh temperature (UHT) thermal treatments. UHT is therefore only applied in the case of liquid products or products with a liquid carrier.

In addition, also known are mechanical treatments especially by application of pressures of several kilobar. Although these treatments enable preservation of the quality of the product, they are only applied to liquid products or products with a liquid carrier; they also require very expensive equipment.

The goal of the present invention is to resolve these drawbacks by proposing a process for the thermal destruction of microorganisms which is capable of preserving to the maximum the quality and the state of the treated medium. The use of high temperature is coupled with a very precise control of the duration of the treatment by means of a very quick rise in temperature and an equally rapid cooling.

One of the objects of the present invention is to propose a volume or surface pasteurization and/or sterilization process consisting of heating under pressure the product to be treated preferably by injection of dry or wet steam so as to reach the pressure "Po", characterized in that one then implements a subsequent cooling by pressure drop down to vacuum. The pressure drop down to vacuum must be controlled between two limits: the most instantaneous possible so as to reduce the cooling time "tr" of the product and, possibly, a rather long duration in order to reduce the phenomena of expansion, texturization or extraction. In fact, it is desirable for numerous alimentary or biological applications, especially for the treatment of fresh products or precooked dishes, to not modify the texture of the products, and to not cause the extraction of the aromas and juices. According to a preferred mode of implementation, the duration of the abrupt pressure drop is a function of the product to be treated, its form, its dimensions and the envisaged quality. It is routinely between instantaneity and 5 seconds.

Advantageously, the initial pressure "Pi" in the treatment chamber prior to the steam injection should be reduced ("Pi"<0.2 bar) so as to reduce the heating temperature rise time "tm" of the products to be treated.

The treatment pressure "Po" is advantageously between 0.8 and 10 bar.

The pressure after the abrupt pressure drop phase is preferably between 1 millibar and 0.6 bar.

According to a specific variant, all volume heating of the pieces of the solid product is avoided or reduced so as to localize the thermal treatment on the surface. One would then use a wet steam of elevated pressure "Po" during a relatively short treatment time.

According to another variant, the initial application of vacuum by reducing the atmospheric or higher pressure of air or a gas to the pressure "Pi" is implemented in a rather abrupt manner so as to reinforce the mechanical effects.

This treatment pertains to various biological products, in powder or solid form, whole or in pieces, untreated, cut up or ground, raw, cooked, completely or partially dehydrated, etc. The complete or partial elimination of the microorganisms is often coupled with the partial elimination of the free surface water of products in piece form.

One of the other applications cited here as an example pertains to the hydrothermomechanical treatment of natural plant, cereal or starch-based products in grain form or transformed into powders or in the form of alimentary pastes, etc. The products to be treated and the final products are also solids (grains or pieces), powders or pastes.

This treatment is thus directed to the modification of the structure, the physicochemical characteristics and/or the functional properties. It is implemented in a single operation or in a process encompassing the phases of drying, humidification, softening, abrasion, etc. The operation can, therefore, be implemented as pretreatment, treatment or posttreatment of the products in question.

Known in the state of the art are the classic hydrothermal treatment processes for oven-drying cereals in abraded, husked, semi-husked or unhusked grains, principally rice and wheat, with "natural" water content, rewetted or partially dried. The goal of the oven-drying generally comprises a certain complete or partial gelatinization of the starch without noteworthy modification of the structure, thereby causing a certain amount of cooking of the product.

Also known in the state of the art are the cooking or precooking operations performed in water or steam, under atmospheric or elevated pressure, possibly followed by steps involving complete or partial drying. In none of these classic operations is the cooling implemented by abrupt pressure drop down to a reduced pressure nor are the thermal treatment phenomena coupled with mechanical effects.

In addition, also known are expansion operations intended primarily to modify the texture by means of a hydrothermal treatment followed by an instantaneous pressure drop down to atmospheric pressure (puffing) or to vacuum (controlled instantaneous pressure drop [CIPD]). Both of these processes generate an expansion of the products determined by an expansion rate defined by a volume ratio between the final and initial states greater than 1.5. These two operations employ high temperatures with, in the case of CIPD, precise control of the duration of the treatment.

The present invention is directed to the implementation of hydrothermomechanical treatment operations comprising the oven-drying, cooking or precooking and/or partial or complete gelatinization of cereal products in grain, powder, or paste form or in pieces, enabling the perfectly precise control of the treatment time and thus the use of high temperature levels. The use of high temperature is coupled with a very precise control of the duration of treatment by means of a very rapid temperature elevation and an equally rapid cooling. This invention enables coupling of oven-drying with a microtexturing of the products in question defined by an expansion kept below 1.5.

The treated products are finally packaged immediately or following a partial or complete drying operation. The finished product has, in an irreversible and precisely controlled manner, a modified structure, a particular composition of partially or completely gelatinized starch, mechanical properties, textural properties, functional properties (diffusional properties, etc.) which have been modified so as, for example, to allow a rather short subsequent cooking time. The process proposed in the present invention can act on the product in a rapid, precise and perfectly controlled manner with good preservation of the quality.

The process described in said invention is defined with regard to the various operating parameters as a function of the treated product and the envisaged objective. In the case of cereals (Indica, Basmati, Thai or Japonica rice, etc., hard or soft wheat), the relevant products are complete, semi-husked or husked whole grains, alimentary pastes prepared from cereal semolina or flour, with or without various additives (eggs, butter, etc.), flours, etc.

The hydrothermomechanical treatment intended for the oven-drying of the product, its microtexturing and, more specifically, the gelatinization of its starch, the modification of its proteins, etc., comprises the following steps:

The moisture content of the product is established either by prior humidification or by maintaining its natural level around 10% or its fabrication level (alimentary pastes with a moisture content around 30%) or by prior drying, Application of vacuum to the chamber in which the products to be treated are arranged to a total pressure of the chamber of between 10 and 50 mbar, Application of water column pressure between maximum 1 and 10 bar, Maintenance of the desired pressure for between circa 5 and 30 seconds, An abrupt pressure drop down to vacuum (~150 mbar).

This step is often followed by a postdrying step with hot or cold air to a final moisture content of around 10%. One of the direct results of the treatment is the very noteworthy reduction in the drying time with a simplification of the drying diagram preserving the final quality of the product. Thus, in the case of alimentary pastes, for example, the treatment which is the object of the present invention enables reduction of the shrinkage of the paste during drying and a decrease in the duration of the operation as well as the energy expenses. Thus, the present invention enables better controlled drying after the treatment.

After treatment, the products obtained (grains, flours, pastes, etc.) have novel structures (microexpansion, at an expansion rate lower than 1.5); the macromolecular constituents (proteins, starch, etc.) undergo noteworthy hydrothermal type modifications (example: a precisely controlled gelatinization rate, formation of a new gluten structure, etc.). Thus, the products obtained have novel functional qualities. Their rehydration qualities are enhanced and their cooking time is reduced.

Another application which is also cited here as an example concerns the thermal, thermomechanical or hydrothermomechanical treatment of miscible or nonmiscible mixtures of liquids, plant products (aromatic herbs, etc., whole or cut fruits and vegetables) for the purpose of separating or facilitating the separation of their constituents and compounds, modification of their structure and/or their thermophysicochemical behavior, increasing the value of their solid residues or skin, etc. In the case of oleaginous plants, this treatment causes an immediate separation of the oils or facilitates the pressing of the products and improves the extraction of the oils and fats.

Known in the state of the art in the case of treatment of various plant materials for the purpose of extracting various compounds from them (fats, fragrances, essential oils, active principles, etc.) are the steps of surface debacterization by washing with a bactericidal solution, skinning, separation by solvents or by steam driven hydrothermal treatment, etc. The present invention makes it possible to combine two or more of these steps which results in an improvement in the quality as well as a reduction in the treatment time and the operational costs.

The invention also pertains to the installations for the thermal, thermomechanical and hydrothermomechanical treatment, notably for controlled pasteurization and/or sterilization, extraction of essential oils or aromatic compounds, preparation of the material for an extraction of the fats and other compounds by pressing or solvents, of the type of installation comprising a zone for receiving the products to be treated, with means for depressurization and application of steam pressure in said zone.

The installations according to the invention advantageously have a vacuum tank preferably with a capacity at least 20 times greater than the treatment chamber, with a connection system such as a rapid control valve being intercalated between the treatment zone and the vacuum tank. The vacuum is provided by means of a vacuum pump and condensation systems for vapors and condensates. The connection system flow rate is determined on the basis of the product and the objective to be implemented so as to enable equilibrium of the pressures between the chamber and the vacuum tank with a delay ranging from the possible instantaneity to 5 seconds.

Two lock systems advantageously enable passage of the product from the outside to the inside of the treatment chamber or zone in the case of the first system and passage of the product from the treatment chamber or zone to the outside for its recovery and packaging in the case of the second system. The operation of the installation can thus be relatively continuous.

The invention also pertains to the products obtained directly by the implementation of the envisaged treatment process.

The invention pertains especially to debacterized biological products resulting from a precisely controlled thermal treatment process comprising a step of introducing the products into a hermetic treatment chamber, a step of heating the products arranged in the treatment chamber and a cooling step based on a pressure drop down to vacuum.

The invention also pertains to the cooked or raw products in pieces, with varied moisture content or dehydrated in bulk, prepackaged or packaged, resulting from a treatment according to a debacterization and/or disinfection process by precisely controlled thermal treatment. The invention also pertains to the aromatic compounds obtained by extraction from a product treated according to the process in accordance with the invention.

FIG. 1 shows a schematic view of a treatment installation according to the invention.

The first variant of implementation of the installation shown in FIG. 1 is constituted by a watertight chamber (1) connected to a vacuum tank (2) which has a capacity at least 20 times greater than that of the treatment chamber (1).

The treatment chamber (1) is surrounded by a double envelope (3). The annular space comprised between the two envelopes has connectors (4, 5) for the injection and evacuation of steam. The circulation of steam in the double envelope provides for the heating of the treatment chamber (1) to a temperature of 150° C. A connector enables injection of air or gas into the chamber.

The treatment chamber (1) also has a connector (8) for the injection of steam into the interior of the chamber onto the products to be treated.

The chamber is of circular or elongated form, of pseudorectangular or elliptical section.

One variant of this treatment chamber has a cover (6) which assures watertight closing of the chamber after introduction of the products to be treated.

A second variant of this same chamber has two watertight, quick opening ports for charging and discharging. These ports are either perpendicular or inclined to the axis, in which case they can also possibly be circular.

The bottom of the chamber (2) has a valve (9) that controls communication with the vacuum tank (2). The connection between the treatment chamber (1) and the vacuum tank (2) is by means of a conduit of large section so as to enable an elevated flow rate. The vacuum tank (2) is connected to a vacuum pump.

The products to be treated are introduced on a single tray or on multiple superposed trays into the treatment chamber (1). The products are heated by the steam injected into the chamber under high pressure. After a certain heating time, the valve controlling communication between the vacuum tank (2) and the chamber (1) is then opened and the pressure drops approximately 4 bar in less than 5 seconds.

When the minimum pressure has been reached, the valve enabling injection of air or gas into the treatment chamber is opened and then the connector valve with the vacuum tank is closed again.

Figure 2:
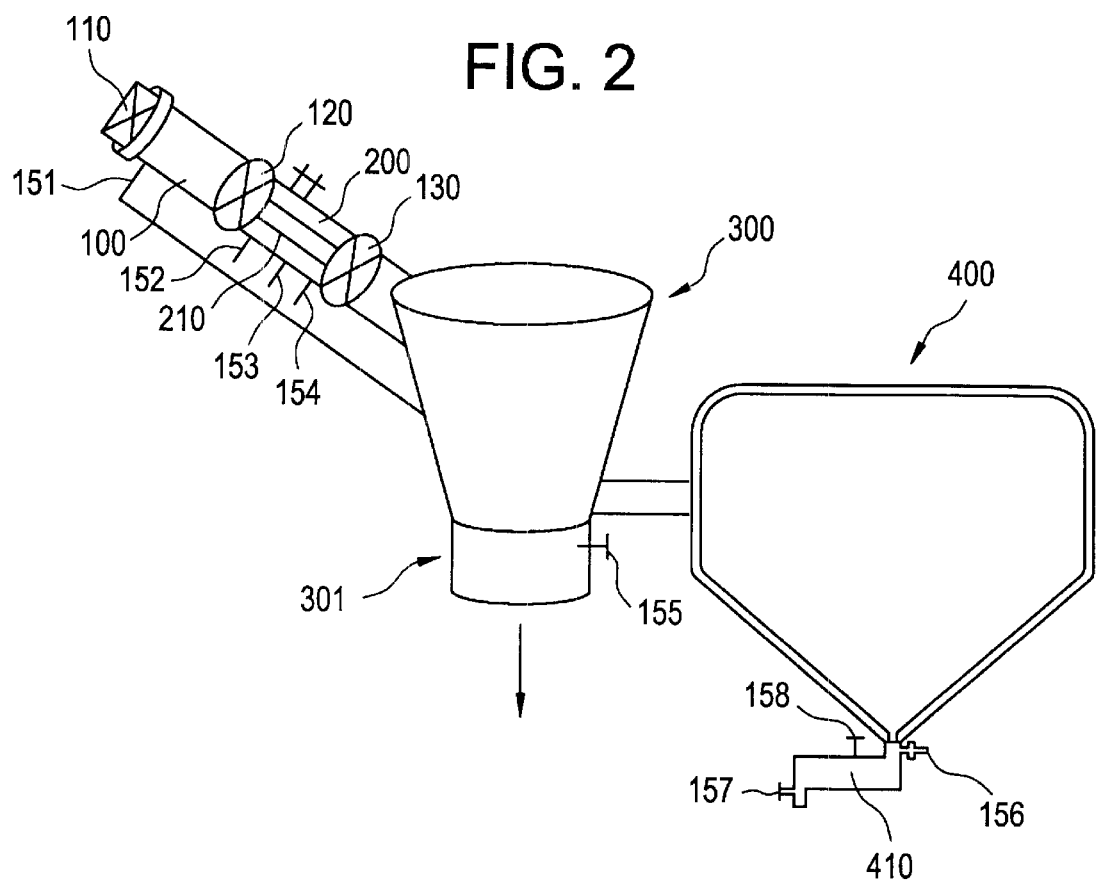
FIG. 2 shows a schematic view of a second variant of implementation of the treatment installation according to the invention.

FIG. 2 shows another variant of implementation which is especially suitable for the extraction of essential oils and aromatic compounds. It comprises the following principal parts:

A loading chamber (100),
A treatment chamber (2),
An intermediary damping chamber (300),
A vacuum tank (400).

The loading and treatment chambers (100, 200) have similar volumes (e.g., 70 liters).

The loading chamber (100) in the example described has a diameter of 35 cm and a height of 60 cm.

The installation has also an intermediary damping receptacle (300) of conical or cylindrical form connected to a receptacle (301) for the recovery of certain extracts from the treated product.

The installation also comprises a vacuum tank (400) of a volume in this case of circa 100 times that of the treatment chamber (200), i.e., 7 m³.

The definition of the intermediary damping receptacle (300), recovery receptacle (301) and vacuum tank (400), their dimensions and their geometric shapes as well as the positions of the cylinders of the chambers (100 and 200) (angle α) depends on the products to be treated, the operating conditions to be employed and the desired quality.

The installation also has multiple solenoid valves:

A first valve (110) V1 between the external loading system and the loading chamber (100),
A second valve (120) V2 between the loading chamber (100) and the treatment chamber (200),
A third valve (130 between the treatment chamber (200) and the intermediary damping chamber (300). Valve (130) is a quick opening valve.

The installation also has various solenoid controlled stopcocks:

A stopcock (151) between the vacuum tank (400) and/or the pump and the loading chamber (100), so as to provide a vacuum in the loading chamber (100) immediately after loading (closure V1) and before the opening of valve (130),
A stopcock (152) for the injection of steam into the treatment chamber (200),
A stopcock (153) for the injection of compressed air (or possibly of a gas under pressure) into the treatment chamber (200),
A stopcock (154) for the possible ejection of condensed water into the treatment chamber (200) before the pressure drop (opening of valve 130),
A stopcock (155) for the possible injection of air or a neutral gas into the recovery tank (301) for the purpose of cooling and/or preserving the treated product.

The treatment chamber (200) has a diameter of 35 cm and in this case is provided with a central tube (210) which has porous walls and a diameter of 15 cm. Its height is 75 cm. The central tube (210) enables treatment of a thinner layer of the product, e.g., 10 cm thick in this case.

Figure 3:
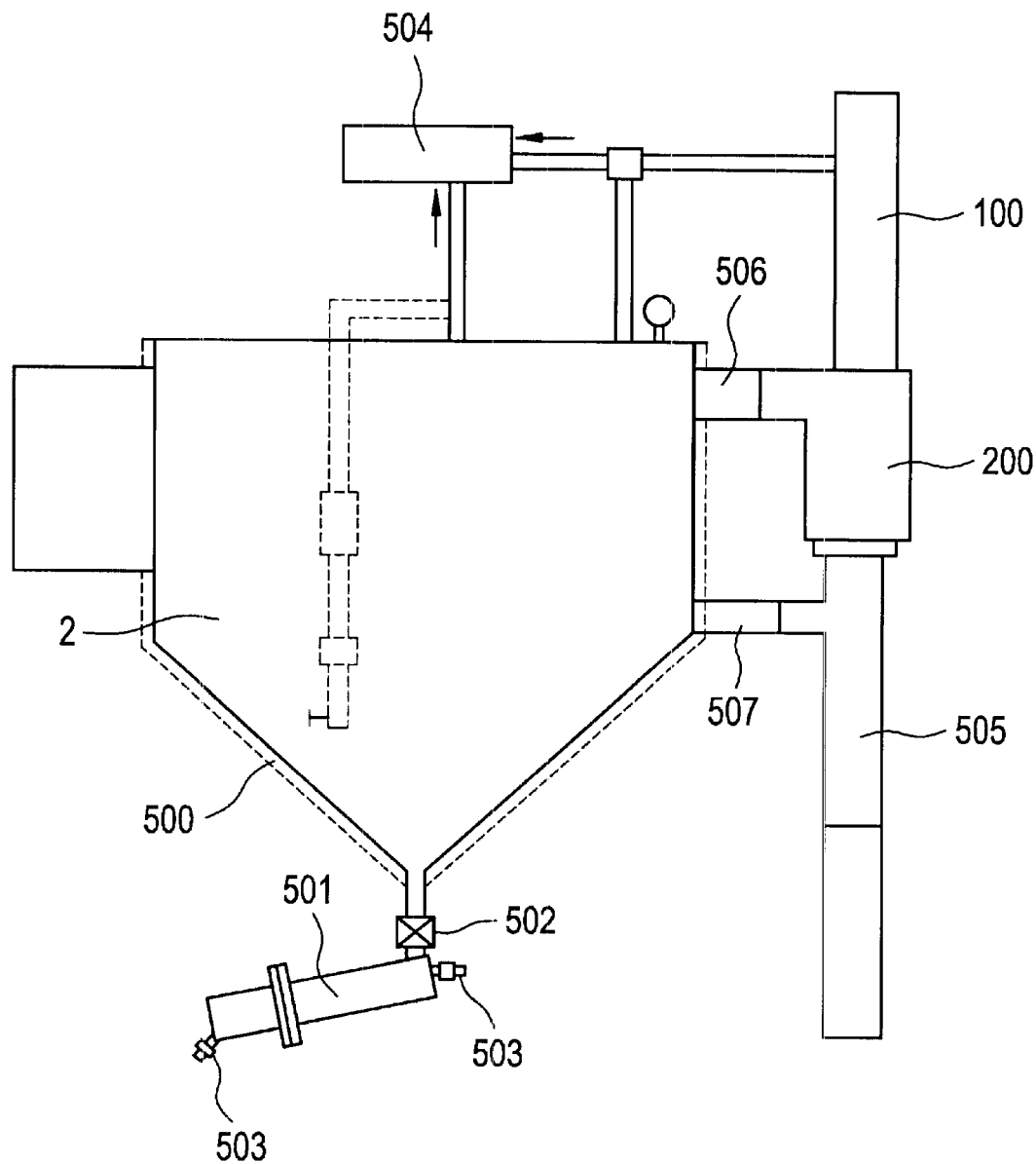
FIG. 3 shows a schematic view of a third variant of implementation of the treatment installation according to the invention.

FIG. 3 shows a schematic view of a variant of implementation. Its vacuum tank (2) is in the form of a double-walled metal cylinder (500), which in this case has a volume 100 times greater than that of the treatment chamber, i.e., 7 m³. The bottom part is formed by a conical surface and a recuperator (501) for condensed liquids. This liquid recuperator (501) is separated from the vacuum tank (2) by a solenoid valve (502) and from the external medium by a solenoid valve (503). A stopcock (503) imposes pressure on the recuperator (501) after closure of solenoid valve (502) and before opening of solenoid valve (502). A condensation system can also facilitate the recovery of the vapors and condensable products and thereby facilitate the application of the vacuum in the tank. vacuum pump (504) of known type contributes to the creation and maintenance of the vacuum in the tank.

The vacuum tank (2) is connected to the treatment chamber (200) by conduits (506, 507). The installation is equipped with pressure and temperature sensors enabling the possibility of control by means of a microcomputer controlling the pressurization and depressurization sequences and controlling duration and temperature inside the chamber. The treatment protocol diagrammed so as to enable the automatic function of the installation.

TABLE 1a

Principal Treatment Phases

| Phase | A | B | D |
|---|---|---|---|
| 1 | Loading | Injection of steam and application of vacuum | Presence of an already treated product |
| 2 | Continuation of loading | Maintenance under pressure | Packaging or discharge of the product (to posttreatment) |
| 3 | Stop loading | Maintenance under pressure | Isolation of the locks |
| 4 | Application of vacuum | Maintenance under pressure | Application of vacuum |
| 5 | Termination of vacuum | Maintenance under pressure | — |
| 6 | — | Maintenance under pressure | — |
| 7 | — | Pressure drop (simultaneous connection with the vacuum and P_atm) and discharge of B into C | Loading the product |
| 8 | — | Maintenance of connection with the vacuum | — |
| 9 | — | — | — |
| 10 | — | Loading | — |

According to a particular variant, a system for the microinjection of air or gas into the chamber (505) enables enhanced cooling of the product after its treatment.

The installation in its diverse variants is especially suitable when the product to be treated is in bulk form. Its recovery can be implemented under a controlled neutral gas or vacuum controlled atmosphere. It also provides for good recovery of the condensates.

The installation is equally adaptable for prepackaged packages as it is for bulk products. It comprises loading and discharging systems employing single or superposed trays.

In the variant of the treatment chamber in elongated form of rectangular or elliptical section, introduction of the product into the chamber and then its extraction to the external atmosphere by means of suitable trays is implemented via two perpendicular ports also of rectangular or elliptical form or, possibly, inclined and of circular form. A T system for carrying, guiding and moving the trays allows the introduction of the trays of products to be treated into the interior of the treatment chamber and the withdrawal of the trays of treated product to the exterior by means of a suitable system such as a set of motorized guide wheels or a conveyor belt.

What is claimed is:

1. A process for precisely controlling thermal, thermomechanical, hydrothermal or hydrothermomechanical treatment of solid or liquid products, comprising:
   heating said products under pressure;
   cooling the products using a controlled, substantially instantaneous, pressure drop process; and
   controlling said pressure drop process to produce a degree of expansion of the product of lower than 1.5.

2. The treatment process according to claim 1, wherein the heating is implemented under a pressure higher than or equal to 0.8 bar.

3. The treatment process according to claim 1, wherein the heating is implemented by injection of wet or superheated steam.

4. The treatment process according to claim 1, wherein the heating is preceded by a step comprising application of reduced pressure in a treatment chamber, with the pressure before heating being lower than 0.2 bar.

5. The treatment process according to claim 1, wherein the cooling is implemented b op to a pressure lower than or equal to 0.5 bar.

6. The treatment process according to claim 1, wherein the pressure drop is determined to cause a degree of expansion of the treated products lower than 1.5.

7. The treatment process according to claim 1, further comprising an initial step of setting operating parameters such that heating temperature level, duration of heating, pressure drop rate to vacuum, and steam pressure as a function of the product to be treated, any organisms and microorganisms to be eliminated and the quality to preserve are optional.

8. The treatment process according to claim 1, wherein the pressure drop rate is determined to maintain the texture of the products.

9. The treatment process according to claim 1, wherein treatment is localized on a surface of the products, coupled with a reduction in free surface water of the products.

10. The treatment process according to claim 1, wherein the products are subsequently packaged under vacuum or under a gas suitable for their preservation.

11. The treatment process according to claim 1, wherein the products after treatment are cooled by a flow of air.

12. The treatment process according to claim 1, wherein the products are subjected to one or more processes selected from the group consisting of debacterization and disinfection.

13. The treatment process according to claim 1, wherein the products are peelable fruits or vegetables.

14. The treatment process according to claim 1, wherein condensable compounds are extracted from the products.

15. The treatment process according to claim 1, wherein liquid compounds are separated from the products.

16. The treatment process according to claim 15, wherein the treatment is implemented by multiple cycles of heating followed by pressure drop to a reduced total pressure.

17. The treatment process according to claim 1, wherein compounds which are volatile at the pressure and temperature after the pressure drop are recovered by one or more of the processes selected from the group consisting of selective condensation and fractionated condensation.

18. The treatment process according to claim 1, wherein products in powder, grain, pieces or solid form, liquids or pastes, raw, cooked or semicooked products, cooked dishes, fruits, vegetables, meats, fish, eggs, of varied moisture content or dehydrated, in bulk or prepackaged form have been debacterized.

19. The treatment process according to claim 1, wherein said controlled substantially instantaneous pressure drop has a duration of about five seconds or less.

* * * * *